United States Patent [19]
Oenick et al.

[11] Patent Number: 5,601,994
[45] Date of Patent: *Feb. 11, 1997

[54] IMMUNOASSAY WITH NOVEL LABELED DRUG HAPTEN ANALOGUES

[75] Inventors: Marsha D. B. Oenick, Rochester; Ignazio S. Ponticello, Pittsford; Susan J. Danielson; Barbara A. Brummond, both of Rochester; David A. Hilborn, Henrietta, all of N.Y.

[73] Assignee: Johnson & Johnson Clinical Diagnostics, Inc., Rochester, N.Y.

[*] Notice: The term of this patent shall not extend beyond the expiration date of Pat. No. 5,298,403.

[21] Appl. No.: 235,114

[22] Filed: Apr. 28, 1994

Related U.S. Application Data

[63] Continuation of Ser. No. 851,436, Mar. 16, 1992, abandoned, which is a continuation of Ser. No. 712,328, Jun. 7, 1991, abandoned.

[51] Int. Cl.$^6$ .................................................. G01N 33/535
[52] U.S. Cl. .......................... 435/7.93; 435/188; 436/816
[58] Field of Search ................................. 435/7.9, 7.93, 435/188; 436/531, 532, 536, 544, 546, 816

[56] References Cited

U.S. PATENT DOCUMENTS

| | | | |
|---|---|---|---|
| 3,875,011 | 4/1975 | Rubenstein et al. | 435/188 |
| 4,065,354 | 12/1977 | Ullman et al. | 195/63 |
| 4,213,964 | 7/1980 | Buckler | 536/4 |
| 4,378,428 | 3/1983 | Farina et al. | 436/528 |
| 4,404,366 | 9/1983 | Boguslaski et al. | 536/5 |
| 4,413,002 | 11/1983 | Wootton | 548/309 |
| 4,447,529 | 5/1984 | Greenquist et al. | 435/4 |
| 4,752,568 | 6/1988 | Danielson et al. | 435/188 |
| 5,096,838 | 3/1992 | Grote et al. | |

OTHER PUBLICATIONS

Anderson et al, CA 109–162790d (1988).
Bacquet et al, CA 104–65419d (1985).
Farina et al, CA 99–2721d (1982).

*Primary Examiner*—Mary E. Ceperley

[57] ABSTRACT

The invention is directed to labeled drug hapten analogues comprising:

(A) a label, of the type used in immunoassays, having an amine or sulfhydryl group;

(B) a drug hapten nucleus selected from barbiturates or hydantoins and (C) a linking chain linking the 3-position of the drug hapten nucleus to the label through a carbonyl bridge.

7 Claims, No Drawings

IMMUNOASSAY WITH NOVEL LABELED DRUG HAPTEN ANALOGUES

This is a continuation of application Ser. No. 851,436, filed Mar. 16, 1992, now abandoned, which is a continuation of application Ser. No. 712,328, filed Jun. 7, 1991, now abandoned.

FIELD OF THE INVENTION

This invention relates to clinical chemistry particularly immunoassays.

BACKGROUND OF THE INVENTION

Immunoassays, which take advantage of natural immunological reactions, have found wide-spread use as analytical techniques in clinical chemistry. Because of the specificity of the reactions, they are particularly advantageous in quantifying biological analytes that are present in very low concentration in biological fluids. Such analytes include, for example, antibodies, therapeutic drugs, narcotics, enzymes, hormones, proteins, etc.

In competitive binding immunoassays, a labeled ligand, including immunocompetent derivatives and analogs of the ligand is placed in competition with unlabeled ligand for reaction with a fixed amount of the appropriate binding material (called a receptor herein). Unknown concentrations of the ligand can be determined from the measured signal of either the bound or unbound (i.e. free) labeled ligand. The reaction proceeds as follows:

ligand+labeled ligand+receptor→ligand-receptor+labeled ligand-receptor.

Conventional labels include radioactive tags, enzymes, chromophores, fluorophores, stable free radicals, and enzyme cofactors, inhibitors and allosteric effectors.

Consistent with the foregoing an immunoassay for drugs, such as phenobarbital and phenytoin, in serum can be based on competition of an enzyme labeled analogue of such drug haptens with the drug in the patient serum for immobilized antibody binding sites.

Specific requirements for the labeled drug hapten analogues (hereafter sometimes LDH) include: 1) at least 65% of the LDH can be bound by excess immobilized antibody; 2) affinity of the LDH for immobilized antibody is such that competition of a fixed amount of LDH with the drug occurs in a therapeutically relevant drug concentration range; and 3) stability of the LDH against hydrolysis of its enzyme label under storage conditions.

Requirements imposed on the drug hapten analogue include: 1) accessibility of the analogue to the immobilized antibody following conjugation with the enzyme label; 2) specific recognition of the LDH analogue by the antibody to the drug; and 3) sufficient reactivity of the analogue with the enzyme label, either directly or following activation of the enzyme or the analogue, under conditions that do not adversely affect enzyme activity.

Glucose oxidase (GOD) and alkaline phosphatase (ALP) enzyme labels coupled to phenobarbital and phenytoin hapten analogues disclosed in U.S. Pat. 4,752,568 gave adequate enzyme labeled analogues for conducting effective competitive immunoassays in the desired format.

The problem is that the labeled phenobarbital and phenytoin analogues disclosed in the above patent were unsatisfactory for conducting competitive immunoassays when the enzyme horseradish peroxidase (HRP) was used as the label. The coupling reactions between such analogues and HRP were both slow and incomplete. Moreover phenobarbital and phenytoin HRP labels were bound very weakly so that much higher concentrations of label or antibody binding sites would be required to give a readable signal.

SUMMARY OF THE INVENTION

The present invention provides an immunoassay method for a drug comprising the steps of:

A. contacting a liquid sample, containing the drug or a derivative thereof, with a labeled analogue of the drug or drug derivative in the presence of antibodies for the drug under conditions that promote the formation of antibody-drug immunocomplexes; and B. determining the quantity of the drug in the liquid by measuring bound or unbound labeled drug analogue; characterized in that the labeled drug analogue comprises:

(i) a label, of the type used in immunoassays, having an amine or sulfhydryl group;

(ii) a drug nucleus selected from a hydantoin nucleus or a barbiturate nucleus and (iii) a linking chain linking the 3-position of the barbiturate or hydantoin nucleus to the label through a carbonyl bridge; wherein the linking chain has about 5 to 40 atoms, consisting of (1) $C_1$ to $C_{10}$ alkylene groups, (2) phenylene groups, and (3) 5 to 7 membered heterocyclic rings joined into the linking group through ring nitrogen atoms, wherein said groups and rings are bonded to each other through chemical groups selected from (a) esters, including thioesters

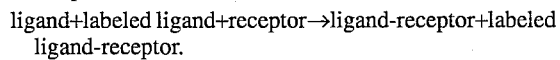

where Z is O or S; (b) amides,

(c) hetero atoms selected from —O—, —S—, and —NR—; wherein R represents $C_1$ to $C_6$ alkyl; and (d) carbonyl, with the proviso that the linking group is other than only a derivative of a saturated or unsaturated monocarboxylic acid having from to 2 to 12 carbon atoms.

The labeled drug hapten analogues useful in the above method include those that conform to the structure:

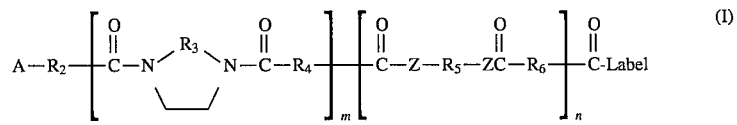

wherein

A represents a hydantoin nucleus of the structure

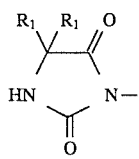

or a phenobarbital barbiturate nucleus of the structure

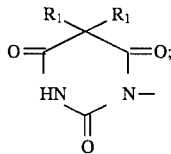

$R^1$ each independently represents hydrogen, alkyl of 1 to 10 carbon atoms, unsubstituted or substituted phenyl;

$R^2$, $R^4$, $R^5$, and $R^6$, each independently represents $C_1$ to $C_{10}$ alkylene or such alkylene groups interrupted with at least one or more ester groups, amide groups, —O—, —S—, and —NR—;

$R^3$ represents $C_1$ to $C_3$ alkylene;

Z represents —O—, —S—, and —NR—, wherein R represents hydrogen or $C_1$ to $C_6$ alkyl, e.g. methyl propyl and hexyl;

m is 0, 1, or 2;

n is 0, 1, or 2;

m+n>0; and the total number of atoms comprised in m, n and $R^2$ is 5 to 40;

LABEL is an enzyme;

and further provided that (i) at least one of the $R^1$ groups is substituted or unsubstituted phenyl; (ii) one of $R^4$, $R^5$, and $R^6$ can be phenylene; (iii) the bracketed components of structure I can appear therein in any order and (iv) the linking group is other than a derivative of a saturated or unsaturated monocarboxylic acid having from to 2 to 12 carbon atoms.

At least 65% of the labeled drug hapten analogues can be bound by an excess of immobilized antibodies to the drugs. The labeled analogues with extended linkers, particularly those having amide bonds in the linking chain are similarly bound by all the immobilized antibody types used in reducing this invention to practice. Also the derivatives having the amide in the extended linker are very stable against hydrolysis.

DETAILS OF THE INVENTION

The drug hapten analogues useful in the immunoassay provided by the present invention are those that comprise:

(a) an active ester group, such as a succinimidoxycarbonyl;

(b) a nucleus selected from hydantoin or barbiturate derivatives; and (c) a linking chain linking the active ester group to the hydantoin or barbiturate nucleus; wherein the linking chain is as previously defined.

More specifically, the preferred new drug hapten analgues useful in this invention are those conforming to the structure:

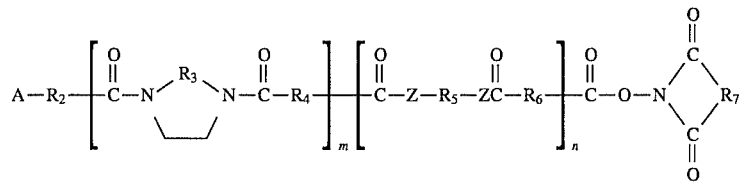

wherein

A represents a hydantoin nucleus of the structure

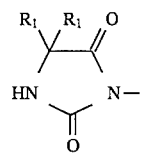

or a barbiturate nucleus of the structure

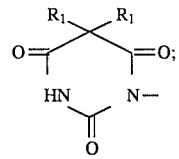

$R^1$, $R^2$, $R^3$, $R^4$, $R^5$, $R^6$, Z, m, and n and the provisos related thereto are as previously defined, and $R^7$ is an ethylene or o-phenylene group. These new drug hapten analogues react with HRP, and other enzymes such as GOD and ALP, faster and more completely, than prior art analogues (b) form covalent bonds with such enzymes without adverse effect on enzyme activity, and (c) the resulting LDH analogues are more readily recognized and tightly bound by antibodies to such drugs.

Hydantoin Drug Hapten Analogues

The novel hydantoin drug hapten analogues are disclosed in copending U.S. patent application Ser. No. 712,329 filed 7 Jun. 1991, abandoned in favor of CIP U.S. Ser. No. 07/851,435 filed Mar. 16, 1992, the same date as the present case.

Several advantages are realized by use of the above hydantoin derivatives. First, it was found that the active esters of these hydantoin derivatives having short linking chains between the hydantoin nucleus and the active ester group were sufficiently reactive with HRP to prepare an acceptable enzyme label for use with some immobilized antibodies. Derivatives with longer linker groups ($R^2$ plus the bracketed groups) of 8 to 20 atoms between the active ester group and the hydantoin nucleus gave labels that could be bound by all immobilized antibodies tested. Linking chains in which each Z is —NR— which with the adjacent carbonyl forms an amide group, are particularly useful in that hydantoin derivatives containing such chains are more resistant to hydrolysis than chains wherein Z is —0— or —S— so that with the adjacent carbonyl it forms an ester group.

Hydantoin analogue Preparatory Examples

The hydantoin analogues can be made according to the following preparations in which phenytoin analogues, a subclass of hydantoin compounds, are made.

1. Preparation of HD 1,5,5-Diphenyl-3-{4-[2-(3-succinimidoxycarbonylpropionyloxy)ethylaminocarbonyl]butyl}hydantoin.

Step 1: preparation of 5,5-Diphenyl-3-[4-(2-hydroxyethylaminocarbonyl)butyl]hydantoin.

Part A: First the Acid Chloride is prepared.

A mixture of 3-(4-carboxybutyl)-5,5-diphenyl-2,4-imidazolidinedione (3.52 g, 0.01 mole) thionyl chloride (20 mL), N,N-dimethylformamide (2 drops) and chloroform (50 mL) was stirred at room temperature for 3 hours. The solvent was removed on a rotary evaporator in vacuo, and this product was used directly in the next Part B.

Part B: The Acid Chloride is reacted with Ethanolamine.

The acid chloride in chloroform (50 mL) was added dropwise over 15 minutes to a mixture of ethanolamine (1.2 g, 0.02 mole) and triethylamine (2.4 g, 0.024 mole) in chloroform (100 mL). The mixture was then heated to 60° C. for 2 hours and stirred to room temperature for 1 hour. The solution was then washed with 5% hydrochloric acid (2×100 mL), washed with saturated sodium bicarbonate solution (100 mL), dried over anhydrous magnesium sulfate, filtered, and the solvent removed on a rotary evaporator. The filtrate was then chromatographed using an aluminum oxide column to give material (3.0 g) showing one spot on TLC. This material was used directly in the next preparation.

Step 2: preparation of 3-{4-[2-(3-Carboxypropionyloxy)-ethylaminocarbonyl]butyl}-5,5-diphenylhydantoin.

The hydroxy compound of Step 1 (3.0 g, 0.0075 mole), succinic anhydride (1.0 g, 0.01 mole), and dimethylaminopyridine (0.9 g, 0.0075 mole) in chloroform (100 mL) were heated at 50°–60° C. for 4 hours and allowed to cool to room temperature over the weekend.

Dichloromethane (300 mL) was added, and the mixture was washed with 5% hydrochloric acid solution (3×100 mL), washed with saturated sodium chloride solution (100 mL), dried over anhydrous magnesium sulfate, filtered, and the solvent removed to give a material that gave one spot on TLC.

Step 3: preparation of HD 1: 5,5-Diphenyl-3-{4-[2-(3-succinimidoxycarbonylpropionyloxy)ethylaminocarbonyl]butyl}hydantoin.

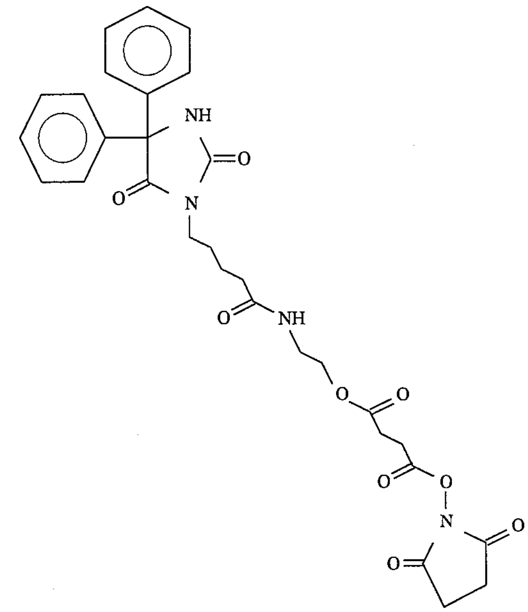

A mixture of the acid from Step 2 (3.0 g, 0.006 mole), N,N'-dicyclohexylcarbodiimide (1.5 g, 0.007 mole), and N-hydroxysuccinimide (0.7 g, 0.006 mole) in chloroform (80 mL) was stirred at room temperature for 20 hours. The mixture was filtered, and the filtrate was concentrated on a rotary evaporator in vacuo. The residue was then chromatographed using silica to give 1.3 g (40% yield).

Anal. calc. for $C_{30}H_{32}N_4O_9$: C, 60.8; H, 5.44; N, 9.45. Found: C 59.6; H, 5.51, N, 8.91

2. Preparation of HD 2: 5,5-Diphenyl-3-{4-[4-(3-succinimidoxycarbonylpropionyl)-1-piperazinylcarbonyl]butyl}-2,4-imidazolidinedione Step 1: preparation of 5,5-Diphenyl-3-(1-piperazinylcarbonylbutyl)hydantoin.

Part A: First, 3-[4-(4-Benzyloxycarbonyl-piperazinylcarbonyl)butyl]-5,5-diphenyl-2,4-imidazolidinedione was prepared.

The acid chloride prepared as described in the preparation of HD 1, supra, Part A (0.01 mole) was added dropwise over 15 minutes to a mixture of benzyl 1-piperazinecarboxylate (2.4 g, 0.011 mole) and triethylamine (2.0 g, 0.02 mole) in chloroform (50 mL). This mixture was stirred at room temperature overnight, and dichloromethane (300 mL) was added. The mixture was washed with 5% hydrochloric acid (2×100 mL), washed with dilute sodium carbonate solution (100 mL), washed with saturated sodium chloride solution (100 mL), dried over anhydrous magnesium sulfate solution, filtered, and the solvent removed on a rotary evaporator in vacuo. The filtrate was then chromatographed to give an oil, 4.3 g (78% yield) which was used directly in the next step.

Part B: The protected amine of Part A (4.8 g, 0,008 mole) and 30–35% hydrogen bromide acetic acid solution (25 mL) was allowed to stir at room temperature for 1.5 hours. This mixture was then poured into diethyl ether (1 L), and the oil which separated was triturated with fresh portions of ether (3×1 L). The oil was dissolved in 10% aqueous sodium hydroxide solution (pH=14) and the aqueous solution extracted with dichloromethane (4×100 mL). The combined organic solution was washed with saturated sodium chloride solution (150 mL), dried over anhydrous magnesium sulfate, filtered, and the solvent removed in a rotary evaporator in vacuo. The filtrate solidifies to give a white solid (2.6 g, 77% yield). This material was used directly in the next step.

Step 2: preparation of 3-{4-[4-(3-Carboxypropionyl)-1-piperazinylcarbonyl]butyl}-5,5-diphenyl-2,4-imidazolidinedione.

A mixture of the amine from Preparation 7 (2.1 g, 0.005 mole) and succinic anhydride (0.54 g, 0.0054 mole) in chloroform (15 mL) was heated for 30 minutes at 50°–60° C. and allowed to stand at ambient temperature for 20 hours. Dichloromethane (150 mL) was added, and the mixture was washed with 5% hydrochloric acid (2×100 mL), saturated sodium chloride solution (100 mL), dried over anhydrous magnesium sulfate, filtered, and the solvent removed on a rotary evaporator in vacuo to give a white solid, 2.5 g (95%) which was used directly in the next step.

Step 3: preparation of HD 2: 5,5-Diphenyl-3-{4-[4-(3-succinimidoxycarbonylpropionyl)-1-piperazinylcarbonyl]butyl}-2,4-imidazolidinedione.

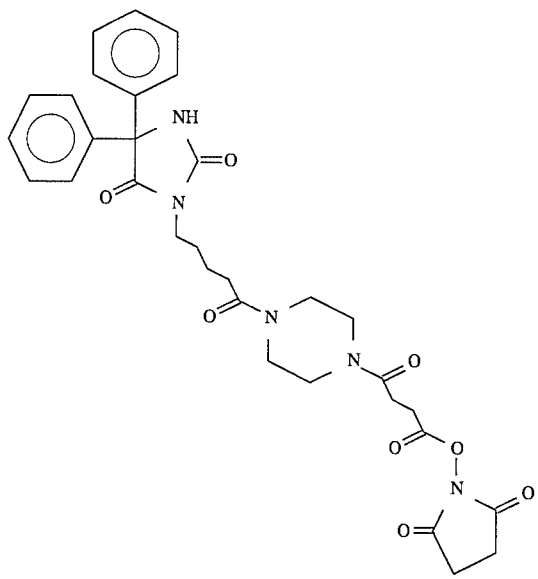

A mixture of the acid from step 2 (1.56 g, 0.003 mole), N,N'-dicyclohexylcarbodiimide (0.64 g, 0.003 mole), and N-hydroxysuccinimide (0.36 g, 0.003 mole) in chloroform (40 mL) was stirred at room temperature over the weekend. The mixture was filtered and the solvent removed from the filtrate on a rotary evaporator in vacuo to give 1.9 g (100% yield). The solid was chromatographed, and the product fraction was dissolved in dichloromethane (200 mL), washed with dilute sodium carbonate solution (2×100 mL), dried over anhydrous magnesium sulfate, filtered, and the solvent removed on a rotary evaporator to give a white solid which gives one spot on TLC.

3. Preparation of HD 3,5,5-Diphenyl-3-{4-[6-(3-succinimidoxycarbonylpropionamido)hexylaminocarbonyl]butyl}-2,4-imidazolidinedione.

Step 1: preparation of 3-[4-(6-Aminohexylaminocarbonyl)butyl]-5,5-diphenyl-2,4-imidazolidinedione.

Part A: preparation of 3-[4-(6-Benzyloxycarbonylaminohexylaminocarbonyl)butyl]-5,5-diphenyl-2,4-imidazolidinedione.

The acid chloride prepared as an intermediate in the preparation of HD 1 was treated with N-benzyloxycarbonyl-1,6-hexanediamine by the procedures described in step 1 in the preparation of HD 2, to give 7.5 g, 85% yield, of the protected amine.

Part B: The protected amine of Part A was treated with hydrobromic acid-acetic acid by the procedures of Step 1, Part B in the preparation of HD 2, to give the free amine which was used in step 3 without purification.

Step 3: preparation of 3-{4-[6-(3-Carboxy-propionamido)hexylaminocarbonyl]butyl)-5,5-diphenyl-2,4-imidazolidinedione.

This compound was prepared using the same procedures as step 2 of the HD 2 preparation.

Step 4: preparation of HD 3: 5,5-Diphenyl-3-{4-[6-(3-succinimidoxycarbonyl-propionamido)hexylaminocarbonyl]butyl}-2,4-imidazolidinedione.

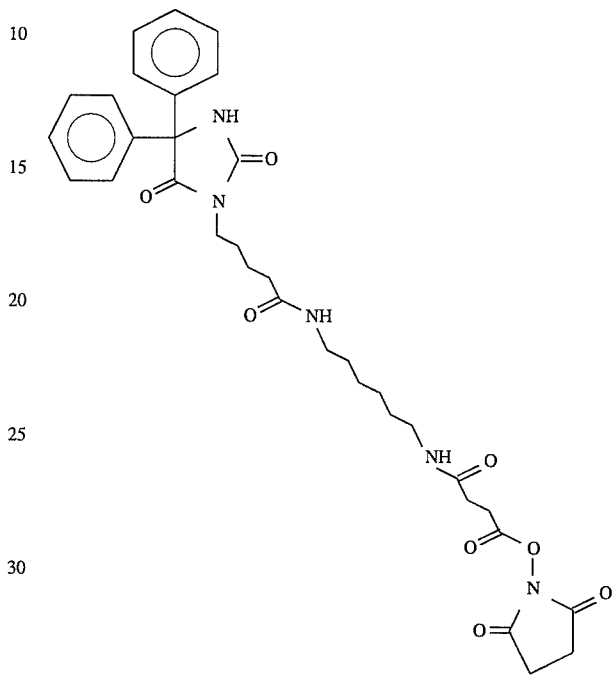

This material was prepared using the procedures of step 3 in the preparation of HD 2 to give 2.6 g (80% yield), mpt 133°–134° C. Anal. Calc. for $C_{34}H_{41}N_5O_8$: C, 63.05; H, 6.38; N. 10.81. Found: C, 62.91; H, 6.41; N, 10.69.

Barbiturate Drug Analogues

The following preparatory examples 4 to 8 illustrate the preparation of the barbiturate drug hapten analogues for phenobarbital. The analogues are generally prepared by (1) condensing a barbiturate derivative such, as phenobarbital, with an omegahaloalkanecarboxylate ester, (2) saponifying the ester to the corresponding acid, (3) conversion of the acid to the corresponding acid chloride and (4) condensation of the acid chloride with N-hydroxysuccinimide, or to further lengthen the linking chain, with a diamine, diol, or aminoalcohol having one of the amine or hydroxy groups blocked, (5) deblocking, condensation with a dicarboxylic acid such as succinic acid, and then condensation with the N-hydroxysuccinimide to produce the analogue.

If desired, the condensation with a half-blocked diamine, diol, or aminoalcohol, and then another diacid can be repeated once or twice more to further lengthen the linking chain. However, the same can be accomplished with fewer steps by using longer chained diacids, diols, diamines, amino alcohols, or haloalkanecarboxylate esters.

4. Preparation of PB 1: 5-Ethyl-5-phenyl-1-{4-[4-(3-Succinimidoxycarbonylpropionyl)-1-piperazinyl-carbonyl]butyl}-2,4,6(IH,3H,5H)pyrimidinetrione Step 1: Preparation of 5-ethyl-6-hydroxy-3-(4-methoxycarbonylbutyl)-5-phenyl-2,4(3H, 5H)-pyrimidinedione A mixture of phenobarbital (46.5 g, 0.2 mole) and tetrabutylammonium hydroxide (500 mL, 0.2 mole of 0.4M in water) in dichloromethane (500 mL) was prepared and to it was added methyl 5-bromovalerate (39.0 g, 0.2 mole). The reaction mixture was stirred vigorously overnight (20 hrs). To this mixture was added saturated sodium chloride solution (100 mL), the organic layer was separated, and the aqueous solution was washed with dichloromethane (2×100 mL). The combined organic solution was washed with saturated sodium chloride solution (100 mL), dried over anhydrous MgSO₄, filtered, and the solvent removed.

Step 2: Preparation of 3-(4-Carboxybutyl)-5-ethyl-6-hydroxy-5-phenyl-2,4(3H,5H)-pyrimidinedione The 5-ethyl-6-hydroxy-3-(4-methoxy-carbonylbutyl)-5-phenyl-2,4 (3H,5H)-pyrimidinedione ester (54.0 g, 0.156 mole) of step 1 in dioxane (500 mL), concentrated hydrochloric acid (55 mL), and water (55 mL) was heated at reflux for 4 hrs and at room temperature overnight. The dioxane was removed under reduced pressure, and saturated sodium chloride solution (250 mL) and dichloromethane (400 mL) were added to the residue. The organic layer was separated, and the aqueous solution was extracted with dichloromethane (3×150 mL). The combined organic solutions were washed with saturated sodium chloride solution (200 mL), dried over anhydrous MgSO₄, filtered, and the solvent removed. To the residue was added diethyl ether, and the mixture was placed in a freezer at −16° C. over the weekend, and then filtered.

Step 3: Preparation of 1-(4-chlorocarbonyl-butyl)-5-ethyl-5-phenyl-2,4,6(1H,3H,5H)-pyrimidinetrione A mixture of the acid (6.6 g, 0.2 mole) from preparation 2, thionyl chloride (50 mL), N,N dimethylformamide (2 drops), and chloroform (80 mL) was stirred at room temperature for 1.5 hrs. The solvent was removed on a rotary evaporator in vacuo, and this product was used directly in the next step 4.

Step 4: Preparation of 1-[4-(4-Benzyloxy-carbonyl-1-piperazinylcarbonyl)butyl]-5-ethyl-5-phenyl-2,4,6(1H,3H,5H)-pyrimidinetrione The acid chloride of step 3 (0.2 mole) in chloroform (75 mL) was added dropwise over 15 minutes to a mixture of benzyl 1-piperazinecarboxylate (6.0 g, 0.030 mole) and triethylamine (4.0 g, 0.04 mole) in chloroform (100 mL). This mixture was stirred at room temperature for 20 hrs, and dichloromethane was then added (300 mL). The mixture was washed with 10% hydrochloric acid solution (3×100 mL), washed with saturated sodium chloride solution (100 mL), dried over anhydrous magnesium sulfate, filtered, and the solvent removed. The residue was then chromatographed on SiO₂ to give a solid.

Step 5: Preparation of 5-Ethyl-5-phenyl-1-[4-(1-piperazinylcarbonyl)butyl]-2,4,6-(1H,3H,5H)pyrimidinetrione Hydrobromide The protected amine from preparation 4 (6.5 g, 0.012 mole) and 30–35% hydrogen bromide-acetic acid solution (30 mL) was allowed to stir at room temperature for 1.5 hrs. The mixture was then poured into ethyl acetate (2 L), stirred for 1 hr, filtered, and the solid washed with 500 mL ethyl acetate.

Step 6: Preparation of 1-{4-[4-(3-Carboxypropionyl)-1-piperazinyl-carbonyl]butyl}-5-ethyl-5phenyl-2,4,6(1H,3H,5H)-pyrimidinetrione The amine of step 5 (4.8 g, 0.01 mole), succinic anhydride (1.2 g, 0.012 mole), and triethylamine (2.2 g, 0.02 mole) in chloroform (150 mL) were heated for 30 min at 50°–60° C. (hot water) and allowed to stir at ambient temperature for 16 hrs. Dichloromethane (200 mL) was added, the mixture was washed with 10% hydrochloric acid solution (3×100 mL). saturated sodium chloride solution (100 mL), dried over anhydrous magnesium sulfate, filtered, and the solvent removed on a rotary evaporator in vacuo to give a white solid, 3.3 g (66%). This material was chromatographed using a SiO₂ column to give a white solid.

Step 7: Preparation of 5-Ethyl-5-phenyl-1-{4-[4-(3-Succinimidoxycarbonylpropionyl)-1-piperazinylcarbonyl]butyl}-2,4,6(1H,3H,5H)pyrimidinetrione

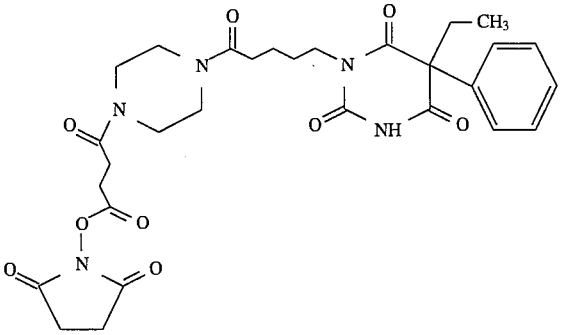

A mixture of the acid from step 6 (3.4 g, 0.007 mole), N,N'-dicyclohexylcarbodiimide (1.6 g, 0.008 mole), and N-hydroxysuccinimide (1.0 g, 0.008 mole) in chloroform (75 mL) was stirred at room temperature for 20 hrs. The mixture was filtered, and ethyl acetate (100 mL) was added. The organic solution was washed with water (2×100 mL), saturated sodium chloride solution (50 mL), dried over anhydrous magnesium sulfate, filtered, and the solvent removed on a rotary evaporator under vacuo. A portion of the solid was chromatographed to give a white solid.

5. Preparation of PB 2,5-Ethyl-5-phenyl-2-(4-succinimidoxycarbonylbutyl)-2,4,6(1H,3H,5H)pyrimidinetrione

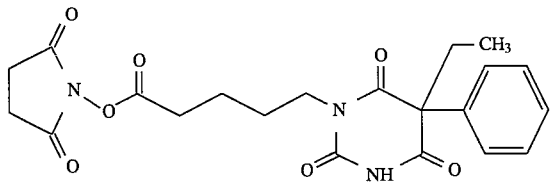

This material was prepared using the procedure of step 7, preparatory example 4 except starting with the acid of step 2. The material crystallizes from ethyl ether/ethyl acetate (1:1) to give a white solid.

6. Preparation of PB 3,5-Ethyl-5-phenyl-1-{4-[2-(3-succinimidoxycarbonylpropionyloxy)ethylaminocarbonyl]butyl}-2,4,6(1H,3H,5H)-pyrimidinetrione Step 1: Preparation of 5-Ethyl-1-[4-(2-hydroxyethylaminocarbonyl)butyl]-5-phenyl-2,4,6(1H,3H,5H)pyrimidinetrione This material was prepared as outlined in step 4 of preparatory example 4 except using 2-hydroxyethylamine in place of the benzyl 1-piperazinecarboxylate.

Step 2: Preparation of 1-{4-[2-(3-Carboxypropionyloxy)-ethylaminocarbonyl]butyl}-5-ethyl-5-phenyl-2,4,6(1H,3H,5H)-pyrimidinetrione A mixture of the product from step 1 (2.9 g, 0.007 mole), succinic anhydride (0.7 g, 0.007 mole), and dimethylaminopyridine (0.9 g, 0.007 mole) in chloroform (100 mL) was heated with hot water (50°–60° C.) for 30 min and then stirred at room temperature for 3 days. Dichloromethane (300 mL) was added, and the mixture was washed with 10% hydrochloric acid solution (2×100 mL), washed with saturated sodium chloride solution (100 mL), dried over anhydrous magnesium sulfate, filtered, and solvent removed to give an oil which was used directly in the next step.

Step 3: Preparation of PB 3,5-Ethyl-5-phenyl-1-{4-[2-(3-succinimidoxycarbonylpropionyloxy)ethylaminocarbonyl]butyl)-2,4,6(1H,3H,5H)-pyrimidinetrione

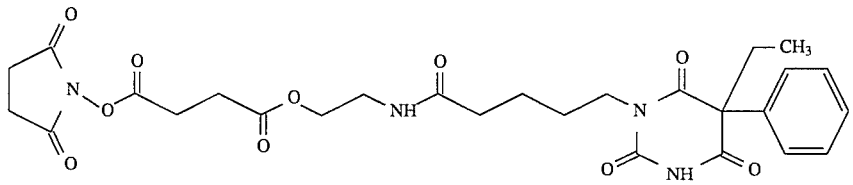

This material was prepared using the procedure outlined in step 7 of preparatory example 4 starting with the acid of step 2 of this example.

7. Preparation of PB 4,5-Ethyl-5-phenyl-1-{4-[3-(3-succinimidoxycarbonylpropionamido)propylaminocarbonyl]butyl}-2,4,6(1H,3H,5H)-pyrimidinetrione Step 1: Preparation of 1-[4-(3-Benzyloxycarbonylaminopropylaminocarbonyl)butyl]-5-ethyl-5-phenyl-2,4,6(1H,3H,5H)-pyrimidinetrione This material was prepared using the procedure outlined in step 4, preparatory example 4, except substituting N-benzyloxycarbonyl-1,3-propanediamine for the benzyl 1-piperazinecarboxylate, and the crude material was used in the next step.

Step 2: Preparation of 1-[4-(3-Aminopropylaminocarbonyl)butyl]-5-ethyl-5-phenyl-2,4,6(1H,3H,5H)-pyrimidinetrione Hydrobromide This material was prepared as in step 5, preparatory example 4 (except starting with the amide of step 1 of this example to give an oil when poured into ethyl ether.

Step 3: Preparation of 1-{4-[3-(3-Carboxypropionamido)propylaminocarbonyl]butyl)-5-Ethyl-5-phenyl-2,4,6(1H,3H,5H)-pyrimidinetrione This material was prepared by the procedure of step 6, preparatory example 4, except starting with the amine from step 2 of this example to give the acid.

Step 4: Preparation of PB 4,5-Ethyl-5-phenyl-1-{4-[3-(3-succinimidoxycarbonylpropionamido)-propylaminocarbonyl]butyl}-2,4,6(1H,3H,5H)-pyrimidinetrione

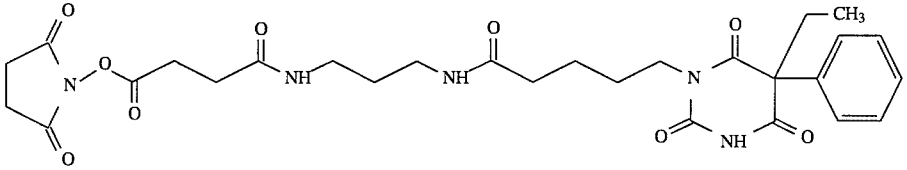

This material was prepared using the procedure of step 7, preparatory example 4 except starting with the acid of step 3 of this example.

8. Preparation of PB 5,5-Ethyl-5-phenyl-1-{4-[6-(3-succinimidoxycarbonylpropionamido)-hexylaminocarbonyl]butyl}-2,4,6(1H,3H,5H)-pyrimidinetrione This compound was prepared by the sequence of reactions of preparation example 7 except substituting N-benzyloxycarbonyl-1,6-hexanediamine for the benzyloxycarbonyl-1,3 propanediamine in step 1, and the respective reaction products thereafter in steps 2, 3, and 4 of preparation example 7.

Labeled Drug Hapten Analogoues

We have prepared new labeled drug hapten analogues of the above prepared barbiturate and hydantoin analogues which are useful in competitive immunoassays for barbiturates and hydantoin drugs, particularly phenobarbital and phenytoin. The labels are those commonly used in immunoassays having an amine or sulfhydryl group commonly used with analytes or analyte analogs in competitive immunoassays such as enzymes, visible dyes, leuco dyes, fluorescent dyes, radioactive materials, etc.

Useful labels are enzymes such as alkaline phosphatase (ALP), glucose oxidase (GOD) and horseradish peroxidase (HRP).

The labeled drug hapten analogues are prepared with a new process comprising the steps of:

1) contacting a label having a nucleophilic group thereon such as an amine or sulfhydryl group, with an excess of a barbiturate or hydantoin drug hapten analogue described supra. Preferably the analogues and the label are dissolved in a water miscible organic solvent such as N,N-dimethylformamide, dimethyl sulfoxide (DMSO) or mixture of solvent and water (buffered) before mixing together; and 2) removing the unused active ester and condensation by-products, preferably by dialysis.

The examples provided hereinafter illustrate the preparation of the new labeled analogues of this invention. The labeled analogues were prepared using phenytoin and phenobarbital drug hapten analogues.

Labeled Hydantoin Analogues

1. Preparation of an Amine Enriched HRP labeled hydantoin HD 1 (containing an extended linker, label AHRP-HD 1, Label A).

HD 1 was dissolved in 1.452 mL dry DMF containing 10 mM 4'-hydroxyacetanilide (DMF 4'-HA).

Amine-enriched HRP was prepared as described in U.S. Ser. No. 540,428, filed Jun. 18, 1990 in the name of Susan J. Danielson and Donald P. Specht, entitled "Amine-Enriched Proteins", the contents of which are expressly incorporated herein by reference. Briefly, dry HRP was dissolved in 0.1M MES buffer, pH 5.5, to achieve a final concentration of $2.5 \times 10^{-6}$ mol (100 mg) in 10 mL of buffer (MES=2-(N-morpholino)ethanesulfonic acid). The protein concentration was determined by $A_{403}$ measurement using the conversion factor $A_{403}$ 1 mg/mL=2.24. The HRP solution was combined with $1.5 \times 10^{-3}$ mol (275 mg) of L-lysine monohydrochloride dissolved in 10 mL of 0.1M MES buffer at pH 5.5. A solution of freshly prepared 1-ethyl-3-(3-dimethylaminopropyl)carbodiimide hydrochloride (EDC, $5 \times 10^{-4}$ mol, 960 mL) in MES buffer was added. The container was capped and mixed overnight at room temperature. The reaction was dialyzed against 0.02M MOPS buffer at pH 7.0 (3 L at 10° C.). The dialysis buffer was changed 3x. MOPS=3-(N-morpholino)propanesulfonic acid.

Prior to reaction, a sample of the amine-enriched HRP was exchanged from MOPS buffer into 0.1M EPPS buffer, pH 8.0, using 30,000 NMWL (nominal molecular weight limit cutoff) Centricells centrifugal ultrafilters. This sample was then diluted to obtain a solution with a final concentration of 10 mg/mL.

The amine-enriched HRP (AHRP) (1 mL) was combined with 500 μL of a 10 mM solution of 4'-hydroxyacetanilide in dimethylformamide (DMF 4'-HA) with vortex mixing and was then placed in a 42° C. water bath. An HD 1 solution prepared by dissolving 21 mg of HD 1 in 1.452 mL of dry DMF 4'-HA solution (500 μL) was added dropwise to the AHRP with vortex mixing so that the molar ratio of phenytoin/HRP was 50/1. The reaction was incubated for 1 hour in a 42° C. water bath with gentle shaking.

The reaction was placed in Spectrapor #2 dialysis tubing along with an additional 0.5 mL of DMF 4'-HA/0.1M EPPS (1:1) used to rinse the reaction container.

The reaction mixture was dialyzed as follows:

a) 1 L DMF 4'-HA/0.1M EPPS. pH 8.0, (1:1) at 42° C. for 1 hr;

b) Dialysis condition a) was repeated 1 time;

c) 2 L 0.1M EPPS, pH 8.0, containing 0.1% BSA at 8° C. for 15 hrs d) 2 L of 0.1M EPPS, pH 8.0, at 8° C. for 3 hours;

e) 3 L of 0.04M tris(hydroxymethyl)aminomethane hydrochloride (Tris HCl)/0.15M NaCl, PH 7.5, at 8° C. for 3 hours; and f) Dialysis condition e) was repeated 1 time for 3 hrs;

Following dialysis, merthiolate was added to 0.02% as a preservative, and the AHRP-HD 1 was stored refrigerated.

2. Preparation of an Amine Enriched HRP labeled HD 2 (containing an extended linker with an amide bond, label AHRP-HD 2, Label B).

HD 2 (15.5 mg) was dissolved in 1.031 mL dry DMF containing 10 mM 4'-hydroxyacetanilide (DMF 4'-HA).

A solution of AHRP (10 mg/mL, 1 mL in 0.1M EPPS, pH 8.0), prepared as described in label Preparatory example 1, was combined with 500 μL of DMF 4'-HA with vortex mixing and was then placed in a 42° C. water bath. The HD 2 solution described above (500 μL) was added dropwise to the AHRP with vortex mixing so that the molar ratio was 50/1. The reaction was incubated for 1 hour in a 42° C. water bath with gentle shaking.

The reaction product was placed in Spectrapor #2 dialysis tubing and dialyzed as follows:

a) 1 L DMF 4'-HA/0.1M EPPS, pH 8.0 (1:1) at 42° C. for 1 hr;

b) Dialysis condition a) was repeated 1 time;

c) 1.5 L 0.1M EPPS, pH 8.0, containing 0.1% bovine serum albumin (BSA) at 8° C. for 1.5 hr;

d) 1.5 L 0.1M EPPS, pH 8.0, at 8° C. for 18 hrs;

e) 1.5 L 0.04M Tris HCl/0.15M NaCl, pH 7.5, at 8° C. for 2 hrs; and f) Dialysis condition e) was repeated 1 time for 4 hrs.

Following dialysis, 0.02% merthiolate was added as a preservative. The labeled hydantoin derivative was stored in a refrigerator.

3. Preparation of AHRP-HD 3 (containing an extended linker with an amide bond label AHRP-HD 3, Label C).

HD 3 (9.2 mg) was dissolved in 1 mL dry DMF containing 10 mM 4'-hydroxyacetanilide (DMF 4'-HA).

A solution of AHRP, prepared as described in label preparatory example 1, was dialyzed into 0.1M EPPS buffer, pH 8.0. The final concentration was determined to be 5.71 mg/ml.

The AHRP (1 mL) was combined with 500 μL of DMF 4'-HA with vortex mixing and was then placed in a 42° C. water bath. The HD 3 solution described above (500 μL) was added to the AHRP dropwise with vortex mixing so that the molar ratio of HD 3/AHRP was 50/1. The reaction was incubated for 1 hour in a 42° C. water bath with gentle shaking. The reaction was placed in Spectrapor #2 dialysis tubing along with an additional 0.5 mL of DMF 4'-HA/0.1M EPPS (1:1) used to rinse the reaction container.

The reaction was dialyzed as follows:

a) 1 LDMF 4'-HA/0.1M EPPS, pH 8.0, (1:1) at 42° C. for 1 hour;

b) dialysis condition a) was repeated 1 time;

c) 1.5 L 0.1M EPPS, pH 8.0, containing 0.1% BSA at 5° C. for 15 hours;

d) 1.5 L 0.1M EPPS, pH 8.0, for 8 hours;

e) 2 L 0.02M 3-morpholinopropanesulfonic acid (MOPS), pH 7.0. at 5° C. for 13 hours; and f) Dialysis condition e) was repeated 2 times.

Following dialysis, merthiolate was added to a concentration of 0.02% as a preservative, and the label was stored refrigerated.

Labeled Barbiturate Drug Hapten Analogues

The following examples demonstrate the preparation of labeled barbiturate drug hapten analogues 4. Preparation of Amine Enriched HRP labeled PB 2; label AHRP-PB 2. Label D PB 2 was dissolved in DMSO to yield a 10.7 mg/mL solution ($1.25 \times 10^{-2}$M). Then 500 µL of this solution was added to amine enriched HRP/DMSO solution (prepared similar to AHRP/DMF) dropwise while vortex mixing. The molar ratio of the phenobarbital/HRP was 50/1.

Incubation was performed at room temperature for 4 hours with shaking at 2400 rpm. The sample was transferred to Spectrapor #2 dialysis tubing along with an additional 1 mL of dialysate to rinse the reaction container. The label was dialyzed into 0.02M MOPS buffer, pH 7.0, at 5°–10° C. This dialysis condition was repeated three times with 2–3 L of buffer each time. Following dialysis, 0.02% merthiolate was added as a preservative, and the label was stored refrigerated.

5. Preparation of Amine Enriched HRP-PB 3; (AHRP-PB3 Label E containing an Extended Linker)

Amine-enriched HRP was exchanged from MOPS buffer into 0.1M EPPS buffer, pH 8.0, using a Centricell centrifugal ultrafilter (30,000 nominal molecular weight limit). This sample was then diluted to 4.6 mL, 0.743 mg/ml.

One mL of the HRP was added to a small vial ($1.85 \times 10^{-5}$M). 500 µL of dimethylformamide, Aldrich 22,705-6, containing 10 mM 4'-hydroxyacetanilide (DMF 4'-HA) was added to the vial, vortexed, and placed in a 42° C. water bath.

Meanwhile, PB-3 was dissolved in DMF 4'-HA to yield a 2.12 mg/ml solution ($3.70 \times 10^{-3}$M). 500 µL of this solution was added to the HRP/DMF 4'-HA solution dropwise while vortex mixing. The molar ratio of the phenobarbital/HRP was 100/1.

Incubation was performed at 42° C. for 1 hour with gentle shaking in a water bath. The sample was transferred to Spectrapor #2 dialysis tubing along with an additional 1 mL of DMF 4'-HA/0.1M EPPS (1:1) used to rinse the reaction container. The reaction was dialyzed as follows:

a) 1 L DMF 4'-HA/0.1M EPPS, pH 8.0 (1:1) at 42° C. for 1 hr;
b) Dialysis condition a) was repeated once;
c) 1.5 L 0.1M EPPS, pH 8.0, containing 0.1% bovine serum albumin (BSA) at 5° C. overnight;
d) 1.5 L 0.1M EPPS, PH 8.0, at 5° C., 8 hrs;
e) 2.0 L 0.02M MOPS, pH 7.0 at 5° C., for at least 8 hrs; and
f) Dialysis condition e) was repeated twice.

Following dialysis, 0.02% merthiolate was added as a preservative, and the label was stored refrigerated.

6. Preparation of an Amine Enriched HRP-PB 1; (Label AHRP-PB 1, Label F, an Active Ester of a Phenobarbital Hapten analogue Containing an Extended Linker with an Amide Bond)

Amine-enriched HRP was prepared and exchanged into 0.1M EPPS buffer, pH 8.0, to yield a, 10 mg/mL solution ($2.5 \times 10^{-4}$M). Label F was made using 5 mL (50 mg) amine-enriched HRP. 2.5 mL DMSO was added slowly, while stirring over a magnetic stir plate. The solution was stirred for 15 minutes at room temperature.

Meanwhile, PB 1 was dissolved in DMSO to yield a 14.9 mg/ml solution. 2.5 mL of this solution was added to the HRP/DMSO solution slowly while stirring. The molar ratio of the phenobarbital/HRP was 50/1.

Incubation was performed at room temperature for 5 hours with shaking at 2400 rpm. The sample was transferred to Spectropor #2 dialysis tubing along with additional dialysate to rinse the reaction container. The label was dialyzed into 0.02M MOPS buffer, pH 7.0, at 5°–10° C. This dialysis condition was repeated three times with 3 L of buffer each time. Following dialysis, 0.02% merthiolate was added as a preservative, and the labels were stored refrigerated.

Immunocompetence

The following tests demonstrate the immunocompetence of the labels 1–6, supra.

1. Immunocompetency of label AHRP-HD 1 (Label A).

In this example, the ability of several immobilized antibodies (DilAs$_8$, DilAs$_9$, DilAs$_{14}$, DilAs$_{16}$, and DilAs$_{21}$) to bind AHRP-HD $_1$ (label A) from label preparatory example 1) is examined.

(a) Polymer bead samples, each sample having one of the above-identified types of antibodies covalently bound thereto were prepared using methods and materials as described in U.S. Ser No. 081,206 filed Aug. 3, 1987 (published EPA 88 307172.2).

(b) The ability of the immobilized antibodies to bind AHRP-HD 1 (label A) was determined as follows:

Each of the various antibody beads were serially diluted with PBS containing 1% BSA to give concentrations between 500 and 0.50 nM antibody binding sites. The bead dilutions were mixed with equal volumes of the label at $10 \times 10^{-11}$M. Following a 1 hour incubation, the beads were pelleted by centrifugation. A sample (100 µL) of the supernatant was mixed with 100 µL of substrate (o-phenylenediamine/H$_2$O$_2$). The rates of color development at 450 nm were compared with those of standards to calculate the amount of phenytoin-HRP label remaining in solution. The amount of label bound to immobilized antibody at the highest antibody concentration tested (250 nM binding sites) is reported.

| % Label Bound at 250 nM Antibody Binding Sites | |
|---|---|
| | Label A (Extended Linker) |
| DilAs$_8$ | 93 |
| DilAs$_9$ | 94 |
| DilAs$_{14}$ | 90 |
| DilAs$_{16}$ | 96 |
| DilAs$_{21}$ | 97 |

These results show that these antibodies recognize very well AHRP-HD 1 Labels (label A).

2. Hydrolytic stability of AHRP-HD 2 (label B)

This example illustrates the hydrolytic stability of a labeled phenytoin derivative of the invention having an amide bond in the linking chain between the label and the phenytoin nucleus AHRP-HD 2, (label B).

Beads having immobilized Kallestad antibodies were prepared as described in U.S. Ser. No. 081,206, filed Aug. 3, 1987 (published EPA 88 307172.2).

AHRP-HD 2 (label B) was diluted to $1 \times 10^{-10}$ M in PBS containing 1% BSA adjusted to pH 7.3 or 8.5. The label was incubated at room temperature for 6 days. The label was tested for binding by immobilized antibody after 2 days and 6 days as follows:

Kallestad 52-2 antibody beads were serially diluted with PBS containing 1% BSA to give concentrations between 500 and 0.50 nM antibody binding sites. The bead dilutions were mixed with equal volumes of labels at $10 \times 10^{-11}$M. Following a 1 hour incubation, the beads were pelleted by centrifugation. A sample (100 uL) of the supernatant was mixed with 100 uL of substrate (o-phenylenediamine/H$_2$O$_2$). The rates were compared with those of standards to calculate the amount of label remaining in solution. The amount of label bound to immobilized antibody at the highest antibody concentration tested (250 nM binding sites) is reported.

| Percent Label Bound at 250 nM Antibody Binding Sites | | |
|---|---|---|
| | Label B (Amide Bond) | |
| | pH 7.3 | pH 8.5 |
| 0 days | 100 | — |
| 2 days | 98 | 99 |
| 6 days | 99 | 100 |

The results show that binding of AHRP-HD 2 (label B) containing the amide bond in the linking chain showed no degradation over this time period. This indicates that label B will resist degradation due to hydrolysis. Such hydrolysis could cause a shift in the assay response with time.

3. Comparison of Phenobarbital-HRP Labels Prepared with Valerate and Extended Linkers In this example, the ability of several immobilized antibodies (Kall 1571 and PbAs9) to bind a label with the valerate linker (label D, AHRP-PB 2) and a label with an extended linker (label F, AHRP-PB 1) were compared.

Immobilized antibody bead samples were prepared as follows:

Polymer beads (30 mg) [poly (styrene-co-p-vinylbenzyl 2-chloroethyl sulfone) (95:5 molar ratio)]were dispersed in 1 mL buffer (0.1M EPPS, pH 8.5) and 0.3 mg of antibody (Kall 1571 or PbAs9) was added. The total volume was 1.5 mL. The mixture was rotated end over end at room temperature for 4 hours. Then 0.3 mL of a 10% solution of BSA was added, and the supernatants were removed and analyzed for unbound antibody using an anti-mouse IgG. The amount of antibody bound to the surface was calculated using ELISA. The pellets were washed 3 times with PBS, pH 7.2, by resuspending in the buffer and centrifuging. The final redispersion was in 1.8 mL of PBS; merthiolate was added to a concentration of 0.02%, and the preparations were stored at 4° C. until use.

The ability of the immobilized antibodies to bind label was determined as follows:

Each of the various antibody beads was serially diluted with PBS containing 1% BSA to give concentrations between 200 and 0.50 nM antibody binding sites. The bead dilutions were mixed with equal volumes of phenobarbital-HRP labels at $10 \times 10^{-11}$M. Following a 1-hour incubation, the beads were pelleted by centrifugation. A sample (100 µL) of the supernatant was mixed with 100 µL of substrate (o-phenylenediamine/$H_2O_2$). The rates of color development at 450 nm were compared with those of standards to calculate the amount of phenobarbital-HRP label remaining in solution. The amount of label bound to immobilized antibody at the highest antibody concentration tested (100 nM binding sites) is reported.

| | % Label Bound at 100 nM Antibody Binding Sites | |
|---|---|---|
| | Label D | Label F |
| Kall 1571 | 41% | 76% |
| PbAs9 | 49% | 73% |

These results indicate that these antibodies show improved recognition of labels prepared with haptens having the extended linking group used in labeled drug hapten analogues provided by the invention. This represents a significant advantage since the hapten with the extended linker allows these antibodies to be considered for development of a phenobarbital enzyme immunoassay.

The immunoassay can be carried out using any suitable label which can be attached to the defined hydantoin and barbiturate derivatives. In addition to the horseradish peroxidase used in preparing the foregoing labeled drug hapten analogues, useful labels include radioactive tags, dyes, fluorescing agents, other enzymes, enzyme substrates, enzyme inhibitors, allosteric effectors, cofactors and other known enzyme modulators. Enzymes, such as glucose oxidase, peroxidases such as horseradish peroxidase and amine-enriched horseradish peroxidase, alkaline phosphatase and galactosidase are preferred labels.

When an enzyme label is used, the substrate for the enzyme is present in the element or added thereto in the developing liquid. The substrate can be added to the element prior to or simultaneously with the liquid sample, or after completion of the binding reaction. It is within the skill of the ordinary worker in clinical chemistry to determine a suitable substrate for a given label. The substrate can be a material which is directly acted upon by the enzyme label, or a material that is involved in a series of reactions which involve enzymatic reaction of the label. For example, if the enzyme label is a peroxidase, the substrate is hydrogen peroxide. Using glucose oxidase as an example, the substrate glucose is generally present in the reagent layer or is added in the developing liquid to yield about 0.01 moles/$m^2$, and preferably from about 0.001 to about 0.1 mole/$m^2$. A worker skilled in the art would know how to adjust the amount of a particular substrate for the amount of enzyme label used in the assay.

When certain labels are used, e.g. enzymes, cofactors, enzyme substrates or enzyme modulators, the reagent layer contains an indicator composition comprising one or more reagents which provide a detectable species as a result of reaction of the label. Preferably, the indicator composition is a colorimetric indicator composition which provides a colorimetrically detectable species as a result of enzymatic reaction of an enzyme-labeled ligand analog with a substrate.

The indicator composition can be a single compound which produces a detectable dye upon enzymatic reaction, or a combination of reagents which produce the dye. For example, when glucose is used as the substrate and glucose oxidase as the enzyme label, the colorimetric indicator composition can include a coupler and oxidizable compound which react to provide a dye. Alternatively, the composition can include a leuco dye and peroxidase or another suitable peroxidative compound which generate a detectable dye as a result of the formation of hydrogen peroxide produced when glucose oxidase converts glucose to gluconic acid. Useful leuco dyes are known in the art and include those, for example, described in U.S. Pat. No. 4,089,747 (issued May 16, 1978 to Bruschi) and U.S. Ser. No. 612,509, filed May 21, 1984 by Babb et al. The particular amounts of the colorimetric indicator composition and its various components are within the skill of a worker in the art.

The immunoassay can be manual or automated. In general, the amount of a ligand in a liquid is determined by taking the element from a supply roll, chip packet or other source and physically contacting a finite area of the spreading layer with a sample of the liquid, e.g. 1 to 100 µl. The finite area which is contacted is generally no more than about 100 $mm^2$.

The amount of ligand is determined by passing the element through a suitable apparatus for detecting the complexed ligand analog directly or the detectable species formed as a result of enzymatic reaction of an enzyme label and a substrate. For example, the species can be detected with suitable radiometric, fluorometric or spectrophotometric apparatus using generally known procedures. In an enzymatic reaction, the resulting product is determined by measuring, for example, the reflection or transmission density or fluorescence in the center of the finite area which was contacted with the test sample. The area which is measured is generally from about 3 to about 5 mm in diameter for competing assays. The amount of ligand in the liquid sample is inversely proportional to the amount of label measured in the center of the finite area. In a preferred embodiment a separate developer step is required in order to maximize separation of complexed ligand from uncomplexed ligand. Generally, label measurement is carried out after from about 5 to about 180 seconds after sample contact and spreading or application of the developing liquid.

EXAMPLES OF THE INVENTION

The following examples demonstrate the immunoassays conveniently on dry immunoassay elements using the labeled drug hapten analgues described above. The examples demonstrate the invention by conducting assays for phenytoin and phenobarbital. It will be clear however that the invention is applicable to other barbiturate and with hydantoin drug derivatives.

In the examples the assay procedures were carried out step-wise according to the following protocol. Ten μL of a sample was spotted on the top surface of a dry immunoassay element of the invention. The element with the now spotted sample was then incubated at 37° C. for 5 minutes. After this period of incubation the element was removed from the incubator and developed with 10 uL of enzyme substrate solution. For the assays used in the examples the label is horseradish peroxidase (HRP) and the substrate used in the developing solution is about 0.3% by weight $H_2O_2$. The developing solution also contains sodium phosphate buffer (pH 6.8) 0.01M, 4'-hydroxyacetanilide (electron transfer agent) 0.005M, diethylenetriaminepentaacetic acid 10 μM and a surfactant. The developing solution causes development of the detectable species. The bound HRP-labeled ligand catalyzes the oxidation of a colorless leuco dye to its colored form. Such dyes are well known in the dry analytical element art and will not be described in detail here. In the examples presented herein the leuco dye is a triarylimidazole. The rate of the catalyzed reaction is measured from the change in reflection density over time at 37° C. Methods and means for measuring reflection density are well known in the analytical arts.

Example 1

Use of a labeled phenytoin analogue in (AHRP-HD 1, Label A) immunoassay for Phenytoin.

The element was prepared using known technology to have the following structure:

| | | Coverage g/m² |
|---|---|---|
| Spreading Layer | Immobilized Kallestad 52-2 Antibody | 0.1 |
| | Particles of poly[m-&p-vinyl- toluene (64:36)-co-methacrylic acid] (98:2 weight ratio (30 μm) | 130 |
| | 4,5-bis(4-dimethylaminophenyl)-2-(4-hydroxy-3,5-dimethoxy-phenyl)imidazole leuco dye | 0.2 |
| | poly(methyl acrylate-co-sodium 2-acrylamido-2-methylpropane-sulfonate-co-2-acetoacetoxy-ethyl methacrylate) (90:4:6 weight ratio) | 2.58 |
| | N-[tris(hydroxymethyl)methyl]-2-aminoethanesulfonic acid; (pH 7.0) | 0.219 |
| | dimethyl sulfoxide | 1.8 |
| | 5,5-dimethyl-1,3-cyclohexane-dione | 0.05 |
| | Zonyl ® FSN nonionic surfactant (DuPont) | 0.054 |
| Gelatin Layer | hardened gelatin | 10 |
| | 4'-hydroxyacetanilide | 0.15 |
| | N-[tris(hydroxymethyl)methyl]-2-aminoethanesulfonic acid; (pH 7.0) | 0.68 |
| | Triton ® X-100 nonionic surfactant (Rohm & Haas) | 0.02 |
| | Poly(ethylene terephthalate) Support | |

A series of human serum based calibrators containing phenytoin and a AHRP-HD 1 (label A) was prepared. Lyophilized serum based calibrators (BioRad) were rehydrated with 3 mL of deionized water. The concentration of phenytoin varied from 0.5 to 128 μg/ml. Label A was added to give a final concentration of 1 nM.

The series of phenytoin standards (10 μL aliquots) was spotted onto the spreading layers of a series of identical analytical elements having the above configuration. After 5 minutes incubation at 37° C., a developing solution (10 μL) comprising hydrogen peroxide (0.03%), sodium phosphate buffer (0.01M, pH 6.8), 4'-hydroxyacetanilide (5 mM) and diethylenetriaminepentaacetic acid (10 μM) was added to initiate dye formation. After about 1 minute, the reflection density ($D_r$) was measured at the center of the area at 680 nm at 37° C. The $D_r$ values were converted to $D_t$ by the Clapper-Williams transform. The change in $D_t$ over 30 seconds was calculated. The results are shown below:

| Phenytoin, μg/ml | Rate ($D_t$/min) |
|---|---|
| 0.5 | 0.0954 |
| 1.0 | 0.0950 |
| 2.0 | 0.0869 |
| 4.0 | 0.0788 |
| 8.0 | 0.0661 |
| 16.0 | 0.0522 |
| 32.0 | 0.0364 |
| 64.0 | 0.0237 |
| 128.0 | 0.0157 |

The results show that there is a significant change in rates over the desired dynamic range. The therapeutic range is 10–20 μg/ml. This example demonstrates an analytical element useful with the immunoassay method provided by the invention and its use in a competitive binding assay to detect the drug phenytoin.

Example 2

Use of AHRP-HD 2 (Label B) having the extended linker and an amide bond in an immunoassay for phenytoin.

This example demonstrates another analytical element provided by this invention and its use as a labeled hydantoin derivative of the invention in a competitive binding assay to detect the drug phenytoin.

The element was prepared using known technology to have the following structure:

|  |  | Coverage g/m² |
|---|---|---|
| Spreading Layer | Immobilized Kallestad 52-2 antibody | 0.15 |
|  | Particles of poly[m-&p-vinyl-toluene (64:36)-co-methacrylic acid) (98:2 weight ratio) (30 μm) | 130 |
|  | poly(methyl acrylate-co-sodium 2-acrylamido-2-methylpropane-sulfonate-co-2-acetoacetoxy-ethyl methacrylate) (90:4:6 weight ratio) | 0.2 |
|  | N-[tris(hydroxymethyl)methyl]-2-aminoethanesulfonic acid; (pH 7.0) | 0.219 |
|  | dimethyl sulfoxide | 1.8 |
|  | 5,5-dimethyl-1,3-cyclohexane-dione | 0.05 |
|  | Zonyl ® FSN nonionic surfactant (DuPont) | 0.054 |
| Gelatin Layer | hardened gelatin | 10 |
|  | 4'-hydroxyacetanilide | 0.15 |
|  | N-[tris(hydroxymethyl)methyl]-2-aminoethanesulfonic acid; (pH 7.0) | 0.68 |
|  | Triton ® X-100 nonionic surfactant (Rohm & Haas) | 0.02 |
|  | Poly(ethylene terephthalate) Support |  |

A series of human serum based calibrators containing phenytoin and label B (AHRP-HD 2) was prepared. Frozen serum based calibrators contained phenytoin in concentrations from 0 to 70 μg/mL. Label B was added to give a final concentration of 1 nM.

A series of phenytoin standards (10 μL aliquots) was spotted onto the spreading layers of a series of identical analytical elements according to the above configuration. After 5 minutes incubation at 37° C., a developing solution (10 μL) con, rising hydrogen peroxide (0.03%), sodium phosphate buffer (0.01M, pH 6.8), 4'-hydroxyacetanilide (5 mM), and diethylenetriaminepentaacetic acid (10 μM) was added to initiate dye formation. After about 1 minute, the reflection density ($D_r$) was measured at the center of the area at 680 nm at 37° C. The $D_r$ values were converted to $D_t$ by the Clapper-Williams transform. The change in $D_t$ over 30 seconds was calculated. The results are shown below:

| Phenytoin, μg/mL | Rate ($D_t$/min) |
|---|---|
| 0 | 0.0759 |
| 10 | 0.0338 |
| 20 | 0.0293 |
| 40 | 0.0206 |
| 70 | 0.0159 |

The results show that there is a significant change in rates over the desired dynamic range. The therapeutic range is 10–20 μg/ml.

Example 3

Use of labeled phenytoin derivative, AHRP-HD 3 (Label C) having an extended linker prepared from hexanediamine with amide bonds in an immunoassay for phenytoin.

This example demonstrates the use of the analytical element described in Example 2 with a different labeled hydantoin derivative of the invention in a competitive binding assay to detect the drug phenytoin.

A series of human serum based calibrators containing phenytoin and Label C from label preparation Example 3 was prepared. Frozen serum based calibrators contained phenytoin in concentrations from 0 to 70 μg/ml. Label C was added to give a final concentration of 1 nM.

A series of phenytoin standards (10 μL aliquots) was spotted onto the spreading layers of a series of analytical elements identical to that described in example 10 except containing Label C in place of Label B. After 5 minutes incubation at 37° C., a developing solution (10 μL) comprising hydrogen peroxide (0.03%), sodium phosphate buffer (0.01M, pH 6.8), 4'-hydroxyacetanilide (5 mM), and diethylenetriaminepentaacetic acid (10 μM) was added to initiate dye formation. After about 1 minute, the reflection density ($D_r$) was measured at the center of the area at 680 nm at 37° C. The $D_r$ values were converted to $D_t$ by the Clapper-Williams transform. The change in $D_t$ over 30 seconds was calculated. The results are shown below:

| 0 | 0.0872 |
|---|---|
| 10 | 0.0439 |
| 20 | 0.0340 |
| 40 | 0.0255 |
| 70 | 0.0202 |

The results show that there is a significant change in rates over the desired dynamic range.

Example 4

Use of a Phenobarbital-HRP Label Prepared with an Extended Linker in an Enzyme Immunoassay for Phenobarbital This example demonstrates the preparation of an analytical element of this invention and its use in a competitive binding assay to detect the drug phenobarbital.

The element was prepared having the following structure:

|  |  | Coverage (g/m²) |
|---|---|---|
| Spreading Layer | Immobilized Kallestad 1571 Antibody | 0.125 |
|  | Particles of poly[m-&p-vinyltoluene (64:36)-co-methacrylic acid] (92:2 weight ratio) (30 μm) | 130 |
|  | 4,5-bis(4-dimethylaminophenyl)-2-(4-hydroxy-3,5-dimethoxyphenyl)imidazole leuco dye | 0.2 |
|  | poly(methyl acrylate-co-sodium 2-acrylamido-2-methyl-propanesulfonate-co-2-acetoacetoxyethyl methacrylate) (90:4:6 weight ratio) | 2.58 |
|  | N-[tris(hydroxymethyl)methyl-2-aminoethanesulfonic acid; (pH 7.0) | 0.219 |
|  | dimethyl sulfoxide | 1.8 |
|  | 5,5-dimethyl-1,3-cyclohexanedione | 0.05 |
|  | Zonyl ® FSN nonionic surfactant (DuPont) | 0.054 |
| Gelatin Layer | hardened gelatin | 10 |
|  | 4'-hydroxyacetanilide | 0.15 |
|  | N-[tris(hydroxymethyl)methyl]-2-aminoethanesulfonic acid; (pH 7.0) | 0.68 |

| | | Coverage (g/m²) |
|---|---|---|
| | Triton ™ X-100 nonionic surfactant (Rohm & Haas) | 0.02 |
| | Poly(ethylene terephthalate) Support | |

A series of human serum based calibrators containing phenobarbital and a phenobarbital-HRP label (label AHRP-PB 3 or label E from the PB-3 of label preparation 6) was prepared. The concentration of phenobarbital varied from 0 to 80 µg/ml. The phenobarbital-HRP label was added to give a final concentration of 6 nM.

The series of phenobarbital standards (10 µL aliquots) was spotted onto the spreading layers of a series of analytical elements. After 5 min incubation at 37° C., a wash solution (10 µL) comprising hydrogen peroxide (0.03%), sodium phosphate buffer (0.01M, pH 6.8), 4'-hydroxyacetanilide (5 mM) and diethylenetriaminepentaacetic acid (10 µM) was added to wash unbound complex away from the center of the area to which the phenobarbital standards had been applied, and to initiate dye formation. After about 1 minute, the reflection density ($D_r$) was measured at the center of the area at 680 nm at 37° C. The $D_r$ values were converted to $D_t$ by the Clapper-Williams transform. The change in $D_t$ over 30 seconds was calculated. The results are shown below:

| Phenobarbital, µg/mL | Rate ($D_t$/min) |
|---|---|
| 0 | 0.095 |
| 7 | 0.073 |
| 20 | 0.053 |
| 40 | 0.038 |
| 80 | 0.026 |

The results show that there is a significant change in rates over the desired dynamic range. The therapeutic range is 20–40 µg/mL.

Example 5

Use of a Phenobarbital-HRP Label Prepared with an Extended Linker with an Amide Bond in an Enzyme Immunoassay for Phenobarbital This example demonstrates the preparation of an analytical element of this invention and its use in a competitive binding assay to detect the drug phenobarbital.

The element was prepared having the following structure:

| | | Coverage (g/m²) |
|---|---|---|
| Spreading Layer | Immobilized PbAs9 antibody | 0.40 |
| | Particles of poly[m-&p-vinyltoluene (64:36)-co-methacrylic acid] (92:2 weight ratio) (30 µm) | 130 |
| | 4,5-bis(4-dimethylaminophenyl)-2-(4-hydroxy-3,5-dimethoxyphenyl)imidazole leuco dye | 0.2 |
| | poly(methyl acrylate-co-sodium 2-acrylamido-2-methylpropanesulfonate-co-2-acetoacetoxyethyl methacrylate) (90:4:6 weight ratio) | 2.58 |
| | N-[tris(hydroxymethyl)methyl]-2-aminoethanesulfonic acid; (pH 7.0) | 0.219 |
| | dimethyl sulfoxide | 1.8 |
| | 5,5-dimethyl-1,3-cyclohexanedione | 0.05 |
| | Zonyl ™ FSN nonionic surfactant (DuPont) | 0.054 |
| Gelatin Layer | hardened gelatin | 10 |
| | 4'-hydroxyacetanilide | 0.15 |
| | N-[tris(hydroxymethyl)methyl]-2-aminoethane-sulfonic acid; (pH 7.0) | 0.68 |
| | Triton ™ X-100 nonionic surfactant (Rohm & Haas) | 0.02 |
| | Poly(ethylene terephthalate) Support | |

A series of human serum based calibrators containing phenobarbital and a phenobarbital-HRP label (AHRP-PB-1, label F from label preparation 6) was prepared. Frozen serum based calibrators contained phenobarbital in concentrations from 0 to 80 µg/mL. The phenobarbital-HRP label was added to give a final concentration of 8 nM.

A series of phenobarbital standards (10 µL aliquots) was spotted onto the spreading layers of a series of analytical elements. After 5 min incubation at 37° C., a wash solution (10 µL) comprising hydrogen peroxide (0.03%), sodium phosphate buffer (0.01M, pH 6.8), 4'-hydroxyacetanilide (5 mM), and diethylenetriaminepentaacetic acid (10 µM) was added to wash unbound complex away from the center of the area to which the phenobarbital standards had been applied, and to initiate dye formation. After about 1 min, the reflection density ($D_r$) was measured at the center of the area at 680 nm at 37° C. The $D_r$ values were converted to $D_t$ by the Clapper-Williams transform. The change in $D_t$ over 30 seconds was calculated. The results are shown below:

| Phenobarbital, µg/mL | Rate ($D_t$/min) |
|---|---|
| 0 | 0.116 |
| 7 | 0.083 |
| 20 | 0.043 |
| 40 | 0.026 |
| 80 | 0.017 |

The results show that there is a significant change in rates over the desired dynamic range. The therapeutic range is 20–40 µg/mL.

In the elements of the examples of the invention the labeled drug hapten derivative is spotted on the element with the sample. Alternatively the labeled drug hapten analogue could be gravure coated over the element spreading layer.

The invention has been described in detail with particular reference to preferred embodiments thereof, but it will be understood that variations and modifications can be effected within the spirit and scope of the invention.

What is claimed is:

1. An immunoassay method for a hydantoin or a barbiturate drug comprising the steps of:

A. contacting a liquid sample containing the drug, with a labeled analog of the drug in the presence of immobilized antibodies for the drug under conditions that promote the formation of antibody-drug immunocomplexes;

separating bound labeled drug analog from unbound labeled drug analog;

B. contacting bound labeled drug analog or unbound labeled drug analog with a developer solution; separating bound labeled drug analog from unbound labeled drug analog; and C. determining the quantity of the drug in the liquid by measuring bound labeled or unbound labeled drug analog; wherein the labeled drug analog conforms to the structure:

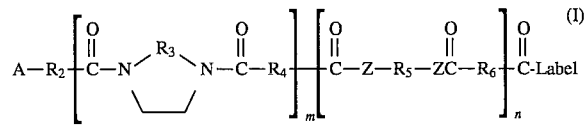

wherein

A represents a hydantoin nucleus of the structure

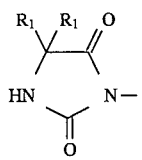

or a barbiturate nucleus of the structure

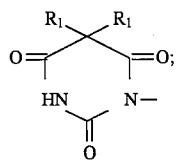

wherein $R_1$ each independently represents hydrogen, alkyl of 1 to 10 carbon atoms, or phenyl;

$R_2$ represents $C_1$ to $C_{10}$ alkylene or such alkylene groups interrupted with at least one or more ester groups, amide groups —O—, —S— or —NR—, wherein R represents hydrogen or $C_1$ to $C_6$ alkyl;

$R_4$, $R_5$ and $R_6$, each independently, represent $C_1$ to $C_{10}$ alkylene or such alkylene groups interrupted with ester groups, amide groups, —O—, —S— or —NR—, wherein R represents hydrogen or $C_1$ to $C_6$ alkyl;

$R_3$ represents $C_1$ to $C_6$ alkylene;

Z represents —O—, —S— or —NR—, wherein R represents hydrogen or $C_1$ to $C_6$ alkyl;

Label represents an enzyme m is 0, 1 or 2;

n is 0, 1 or 2;

m +n >0; and further provided that (i) at least one of the $R_1$ groups is phenyl; and (ii) the bracketed components of structure I can appear therein in any order and wherein, the linking group is other than a derivative of a saturated or unsaturated monocarboxylic acid having from 2 to 12 carbon atoms.

2. An immunoassay element containing a labeled drug analogue according to claim 1.

3. The method of claim 1 in which the labeled drug analogue conforms to the structure wherein:

each $R_1$ independently represents ethyl or phenyl;

$R_2$ represents butylene;

$R_4$, $R_5$ and $R_6$ each independently represents ethylene or hexylene;

Z represents —O— or —NH—; and

Label represents enzyme.

4. The immunoassay of claim 1 wherein the label is horseradish peroxidase (HRP) or amine enriched horseradish peroxidase (AHRP), the labeled drug is a labeled phenytoin or phenobarbital analogue and the linking group connecting the drug hapten analogue to the horseradish peroxidase is selected from the group consisting of:

tetramethylenecarbonyliminohexamethylene-iminocarbonylethylenecarbonyl, tetramethylenecarbonyl-1,4-piperazinylene-carbonylethylenecarbonyl, and tetramethylenecarbonyliminoethyleneoxy-carbonylethylenecarbonyl.

5. The method of any one of claims 3, 4, or 1 when carried out on an immunoassay element.

6. The immunoassay method of claim 1 wherein the structure

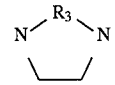

in the linking chain is selected from the group consisting of 1,4-piperazinylene; and 1,3-imidazolidinylene.

7. An immunoassay element having a layer, zone or coating containing a labeled drug analog conforming to the structure:

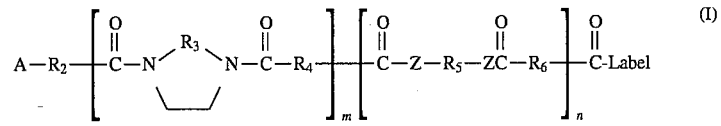

wherein

A represents a hydantoin nucleus of the structure

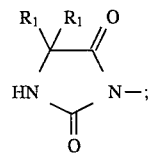

or a barbiturate nucleus of the structure

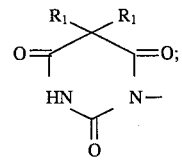

wherein $R_1$ each independently represents hydrogen, alkyl of 1 to 10 carbon atoms, or phenyl;

$R_2$ represents $C_1$ to $C_{10}$ alkylene or such alkylene groups interrupted with at least one or more ester groups, amide groups —O—, —S—, or —NR—, wherein R represents hydrogen or $C_1$ to $C_6$ alkyl;

$R_4$, $R_5$ and $R_6$, each independently, represents $C_1$ to $C_{10}$ alkylene or such alkylene groups interrupted with ester groups, amide groups, —O—, —S—, or —NR—, wherein R represents hydrogen or $C_1$ to $C_6$ alkyl;

$R_3$ represents $C_1$ to $C_3$ alkylene;

Z represents —O—, —S—, or —NR—, wherein R represents hydrogen or $C_1$ to $C_6$ alkyl;

Label represents an enzyme m is 0, 1, or 2;

n is 0, 1, or 2;

m +n >0;

provided that (i) at least one of the $R_1$ groups is phenyl; and (ii) the bracketed components of structure I can appear therein in any order and wherein the linking group is other than a derivative of a saturated or unsaturated monocarboxylic acid having from 2 to 12 carbon atoms.

* * * * *